United States Patent [19]
Carl

[11] Patent Number: 6,116,099
[45] Date of Patent: *Sep. 12, 2000

[54] LIQUID DISPENSING APPARATUS HAVING MEANS FOR LOADING PIPETTE TIPS ONTO FLUID DISPENSING CYLINDERS

[76] Inventor: Richard A. Carl, 30833 Rue Valois, Rancho Palos Verdes, Calif. 90274

[*] Notice: This patent is subject to a terminal disclaimer.

[21] Appl. No.: 08/751,859

[22] Filed: Nov. 18, 1996

[51] Int. Cl.⁷ .................................................. B01L 3/02
[52] U.S. Cl. .................................. 73/864.14; 73/863.32; 73/864.17
[58] Field of Search ........................... 73/863.32, 863.31, 73/864.14, 864.17; 422/100

[56] References Cited

U.S. PATENT DOCUMENTS

| | | | |
|---|---|---|---|
| 4,555,957 | 12/1985 | Frankel et al. | 73/864.14 |
| 4,565,100 | 1/1986 | Malinoff | 73/863.32 |
| 4,936,152 | 6/1990 | Aldred | 73/863.32 |
| 5,226,462 | 7/1993 | Carl | 73/863.32 |
| 5,497,670 | 3/1996 | Carl | 73/863.32 |
| 5,736,105 | 4/1998 | Astle | 73/864.17 |
| 5,827,745 | 10/1998 | Astle | 73/863.32 |

*Primary Examiner*—Hezron Williams
*Assistant Examiner*—Chad Soliz
*Attorney, Agent, or Firm*—Irving Keschner

[57] ABSTRACT

Fluid dispensing apparatus having a loading/stripping plate movable by vertical shafts connected thereto and having a pair of pins on its interior surface for engagement with slots formed on the upper edges of a pipette tray carrier. A standard pipette tip box, with pipette tips therein, is positioned within the tray carrier. When the dispensing apparatus is moved into position on a table about the tray carrier, the loading/stripping plate moves downwardly to engage the tray carrier. The loading/stripping plate is then moved upwardly causing the pipette tips to engage corresponding dispenser cylinders supported in a cylinder plate connected to the shafts. After the pipette tips are loaded to the cylinders, the stripping plate moves downwardly, stripping the pipette tips from the pipette box and returning the tray carrier to the table. The stripper plate includes box strippers to push the box away from the pipette tips that are fixed to the cylinders during the loading cycle and a progressively thicker recess on its bottom surface which allows the pipette tips to be progressively stripped from the cylinders during the unloading cycle.

10 Claims, 3 Drawing Sheets

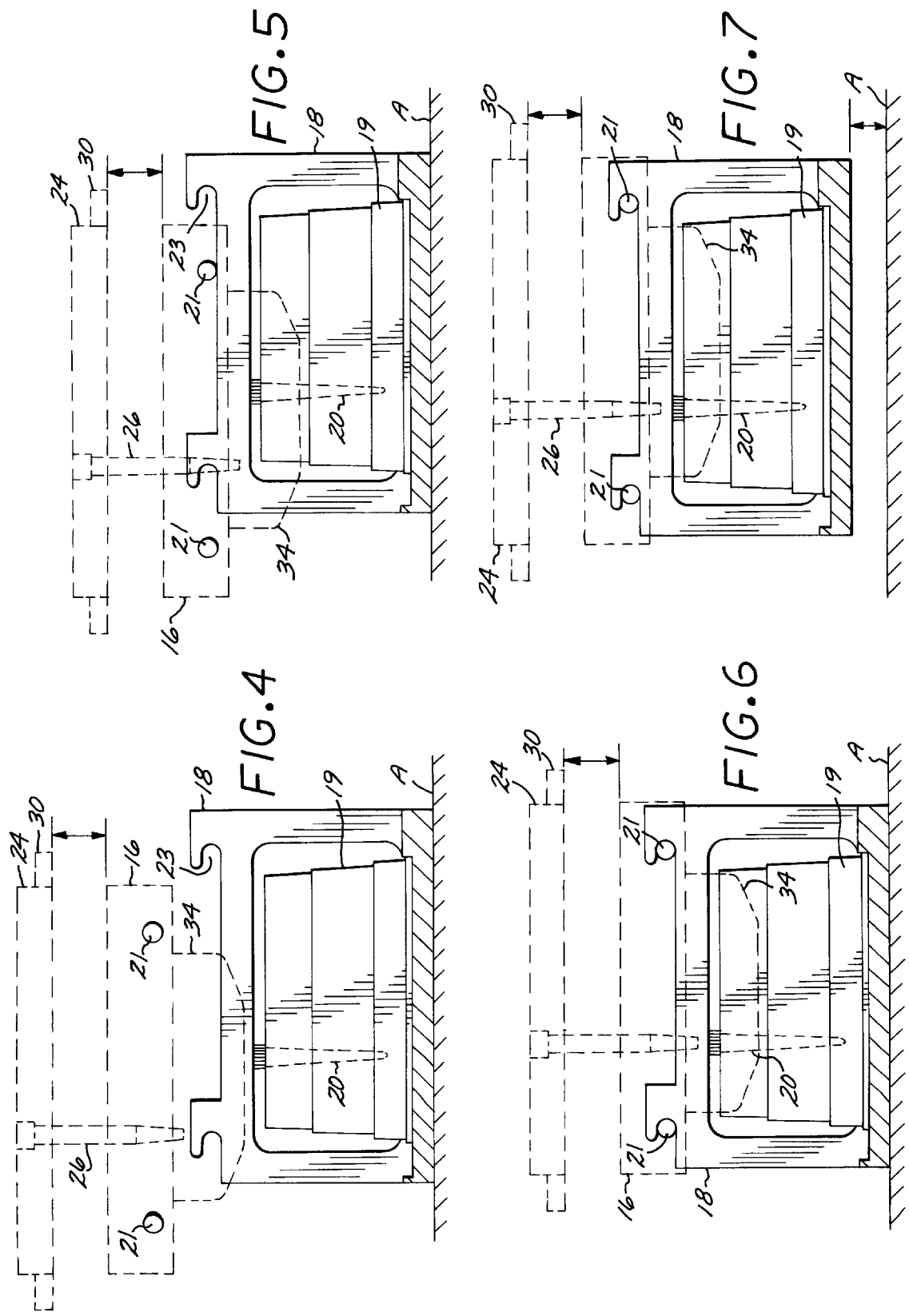

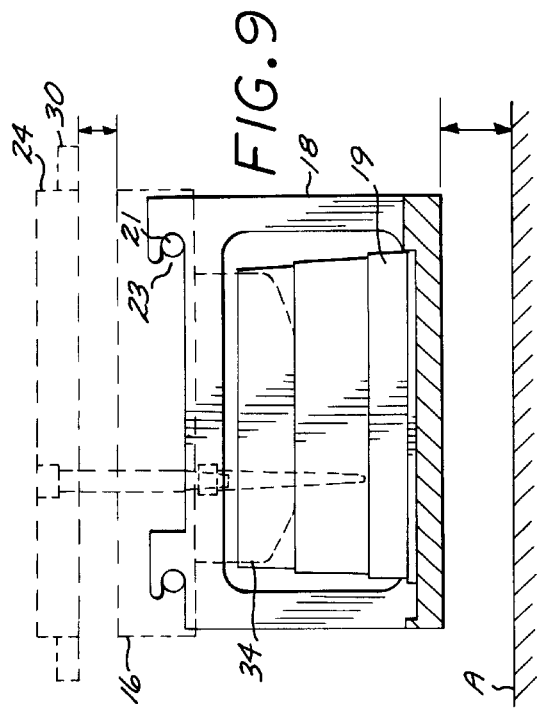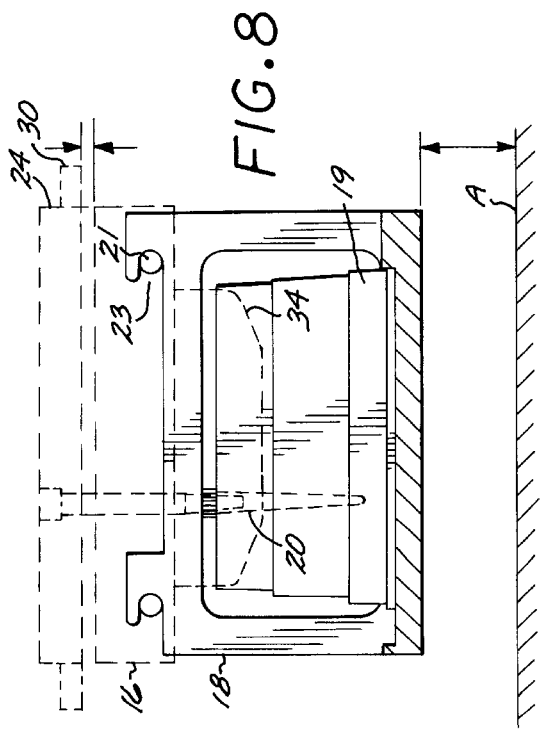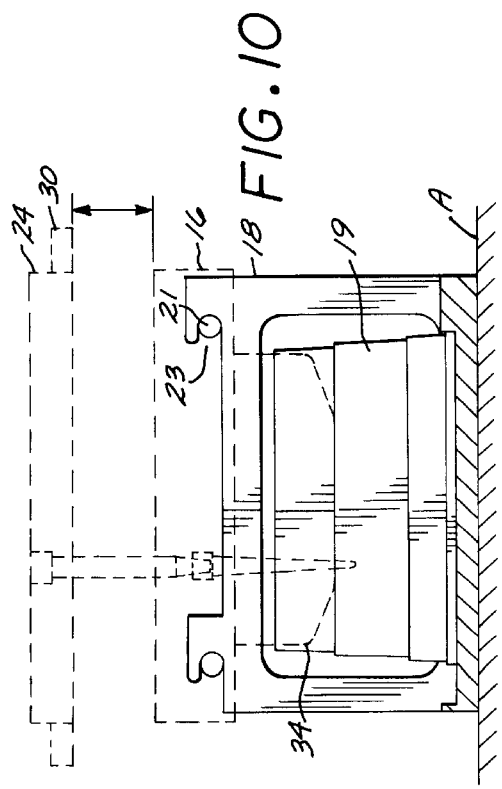

LIQUID DISPENSING APPARATUS HAVING MEANS FOR LOADING PIPETTE TIPS ONTO FLUID DISPENSING CYLINDERS

BACKGROUND OF THE INVENTION

1. Field of the Invention

The present invention provides apparatus for dispensing controlled amounts of liquid into receptacles, the apparatus including improved means for loading disposable pipette tips onto fluid loading/dispensing cylinders.

2. Description of the Prior Art

U.S. Pat. No. 5,497,670 issued Mar. 12, 1996, the subject matter set forth therein invented by the inventor of the present invention, discloses an improved dispensing head apparatus including means for loading pipette tips carried by a pipette plate onto liquid dispensing cylinders, the loading force being maintained during the apparatus operation cycle, thus preventing contamination. The pipette tips are manually placed on the tip plate, the plate sliding within the dispensing apparatus.

Although the pipette tip plate holder described in the aforementioned patent provides many advantages when used with the apparatus described therein, there are certain disadvantages associated with its use. In particular, there is a possibility that the pipette tip box may become contaminated. Most importantly, the pipette tip plate configuration is not easily adapted for robotic operation or automation.

What is desired therefore is to provide a self contained fluid head dispensing apparatus similar to that disclosed in the aforementioned patent but modified to the extent that the pipette tip plate disclosed therein is replaced with a more conventional pipette tip carrier which is less expensive, is less likely to be contaminated and wherein the carrier is easily adapted for robotic operation or automation.

SUMMARY OF THE PRESENT INVENTION

The present invention provides self contained fluid dispensing head apparatus wherein a conventional pipette tip tray carrier is utilized to furnish pipette tips, carried in a standard pipette tip box, to the apparatus dispensing cylinders and wherein means are provided to engage the tray carrier in a manner whereby the pipette tips are loaded on the dispensing cylinders.

The dispensing apparatus comprises a plurality of operating stations arranged to be supported on four vertically extending shafts. The tray carrier engaging means is positioned at the lower end of the apparatus and comprises a loading/stripping plate movable up and down along the four vertical shafts and having a pair of pins on its interior surface for engagement with mating hooks, or slots, formed on the upper edges of the tray carrier. A standard pipette tip box, with pipette tips therein, is positioned within the tray carrier. When the dispensing apparatus is moved into the correct position on a deck, or table, above the tray carrier, the loading/stripper plate moves downwardly to engage the tray carrier. The loading/stripping plate is then moved upwardly along the vertical shafts causing the pipette tips to engage corresponding dispenser cylinders supported in a cylinder plate fixedly connected to the shafts. After the pipette tips are loaded to the cylinders, the stripping plate moves downwardly, elongated members formed on the bottom surface thereof stripping the pipette tips from the pipette box and returning the tray carrier to the deck. The head assembly then moves out with the pipette tips loaded and fills and dispenses fluid into microplates located on the deck. After the dispensing operation is completed, the dispensing apparatus is moved to the tray carrier location on the deck, the pipette tips then being progressively stripped from the cylinders by progressively thicker recesses on the bottom surface of the stripper plate, the pipette tips falling into the pipette box for disposal. A robot can be utilized to supply pipette tip boxes at their associated tray carriers at various locations on the deck since manual insertion in the apparatus (a difficult step to automate) is not required.

The present invention thus utilizes the simple, vertically integrated compact liquid head dispensing apparatus invented by the applicant in conjunction with a conventional, relatively inexpensive, pipette tip box and tray carrier, positioning of the latter components on the deck being adaptable to robotic operation or automation.

DESCRIPTION OF THE DRAWINGS

For a better understanding of the invention as well as other objects and further features thereof, reference is made to the following description which is to be read in conjunction with the accompanying drawings wherein:

FIG. 4 is a view along line 4—4 of FIG. 2; and

FIGS. 5 through 10 illustrate the various steps in loading and stripping the pipettes utilizing the apparatus of the present invention.

DESCRIPTION OF THE INVENTION

Figure 1:
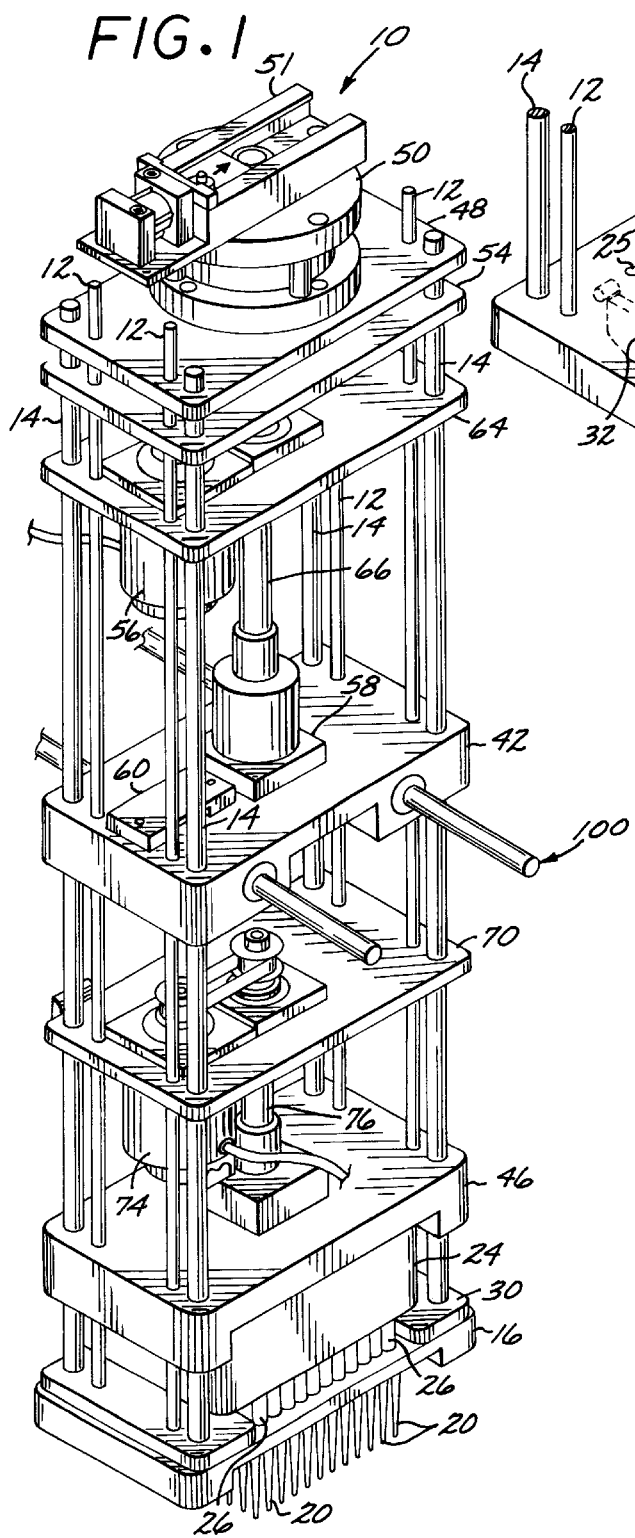
FIG. 1 is a perspective view of the apparatus of the present invention.
Figure 2:
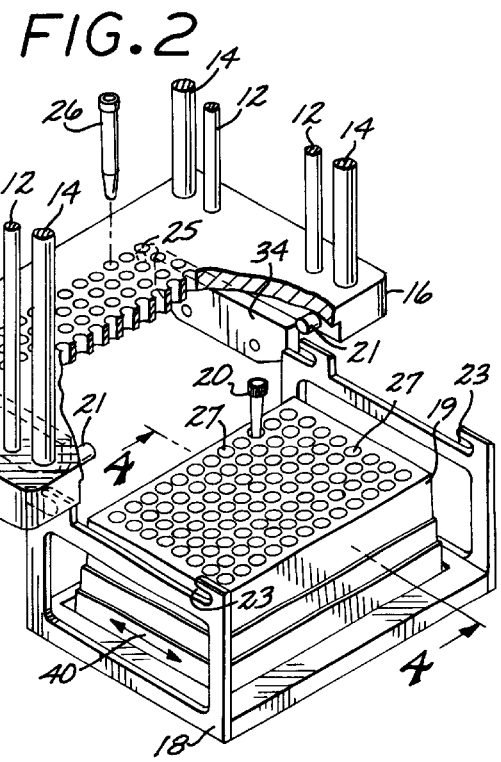
FIG. 2 is a perspective view of the stripping plate portion of the apparatus shown in FIG. 1 and the pipette tip box utilized therewith.
Figure 3:
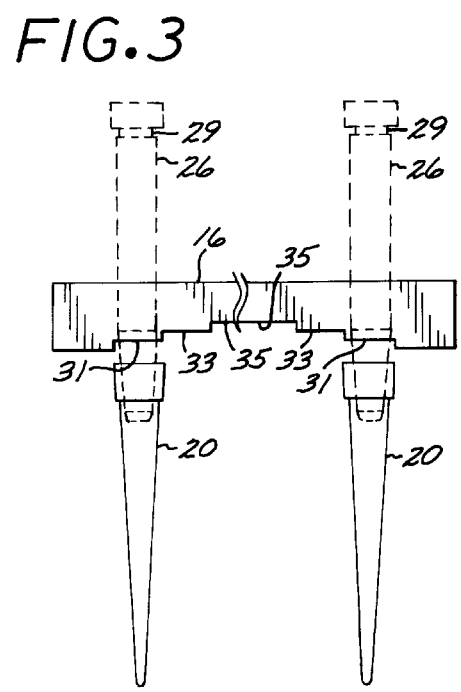
FIG. 3 illustrates the coupling of a dispensing cylinder into a pipette.

Referring now to FIG. 1, a perspective view of the apparatus 10 of the present invention is illustrated. It should be noted that apparatus 10 is similar to the apparatus disclosed in the aforementioned patent and the teachings therein necessary for an understanding of the present invention are incorporated herein by reference. Apparatus 10 comprises a plurality of plate members either fixed on support shafts 12 and 14 or movable in the vertical direction along the support shafts. A loading/stripping plate 16 is attached to shafts 12, arranged to engage pipette tray carrier 18 (FIG. 2), is movable in a vertical direction with respect to the loading cylinders in a manner which will be set forth in more detail hereinafter. Pipette tip tray carrier 18 engages a standard pipette tip box 19 supporting 96 disposable pipette tips 20 (only a single tip 20 is illustrated in FIG. 2). The pipette tips 20, carried by plate 16, are positioned so that they engage corresponding cylinders 26 supported in dispense mechanism 24. Dispense mechanism 24 contains cylinders 26, associated pistons (two pistons 29 are illustrated in FIG. 3) and other components as disclosed in U.S. Pat. No. 5,497,670. A movable piston plate (not shown), part of mechanism 24, is secured to plate 46 which slides up and down along shafts 14.

Cylinders 26 in dispense mechanism 24 are attached to a cylinder mounting plate 30 which is fixed to shafts 14. The pistons are movable in the vertical direction (up/down) within the fixed cylinders 26, the end of the pistons being attached to the movable piston plate. A plate 42 supports the entire apparatus 10 and has a fixed height in elevation relative to the table top, or deck, A (see FIGS. 4–10) on which apparatus 10 is placed.

Shafts 12 are attached to loader plate 48 at the top of apparatus 10 as illustrated. The base of an actuator 50 is mounted on top of loader plate 48 while the actuator arm (not shown) is attached to a fixed plate 54. The extension of the actuator arm causes plate 48 and shafts 12 to rise in relation to plate 54, which in turn causes plate holder 16 and pipette carrier plate 18 to rise in relation to fixed plate 42 along shaft 14 thus loading the tips 20 onto the cylinders 26.

Plate 16 has two functions—the first to load pipette tips 20 to their associated cylinders and remove tip box 19; the second to remove the pipette tips from the cylinders after the dispense cycle.

FIG. 2 is a perspective view of the loading/stripping plate 16 and tray carrier 18, the former fixedly supported to shafts 12 and movable in the vertical direction along shafts 14. The pipette tip box 19, as illustrated, is designed to carry 96 pipette tips although boxes carrying more or less that number can also be utilized.

The vertical, or "Z" axis up/down motion is controlled by stepper motor 56. Slide assembly 58 and 60 mounted on plate 42 all have a fixed height in elevation relative to deck A. The "Z" axis stepper motor plate 64 is fixed to shafts 14. Therefore, as stepper motor 56 turns, it turns lead screw 66, the latter being connected to a lead screw nut which in turn is fixed to plate 58. This motion causes stepper motor plate 64 and all other plates fixed to shafts 14 to move up/down in relationship to the fixed height of plate 42. Since "Z" axis stepper motor plate 64 is fixed to the shafts 14, this plate can move the entire apparatus 10 in an up/down (vertical) direction.

The fluid dispense motion is similar to the operation described above. Fluid dispense stepper motor plate 70 is fixed to the shafts 14, plate 46 having four linear bearings enabling it to slide up/down on shafts 14. Therefore, as fluid dispense stepper motor 74 rotates, it in turn rotates fluid dispense lead screw 76, attached lead screw nut moving plate 46 up/down (vertically) along the shafts 14. The cylinders 26 are part of dispense mechanism 24, dispense mechanism 24 being fixed to plate 30 which in turn is attached to shafts 14. As noted previously, the cylinder pistons are attached to moving piston plate 46. Thus, as the fluid stepper motor 74 rotates, it moves the piston plate 46 up/down in relationship to the fixed cylinders 26 that surround the corresponding pistons.

This motion, in conjunction with the associated seals, causes a vacuum to form in the cylinders 26. This vacuum pulls fluid from a fluid source (not shown) up and into pipette tips 20.

The dispense head apparatus 10 can move up/down in the "Z" axis as set forth hereinabove. The apparatus 10 can also be adapted to move along the "Y" and "X" directions thereby allowing the apparatus 10 to access any microplate positioned on the table top at differing heights. The "Z" axis motion is incorporated in the dispense head apparatus 10 as illustrated. Plate 42, having a fixed height, has linear bearings contained within. These bearings allow apparatus 10 to move along in the "Z", or vertical, direction. An additional stepper motor, lead screw and nuts can be provided to propel apparatus 10 in the "Y" direction along shafts, or rods, 100 (a third "X" axis may also be incorporated in the design allowing apparatus 10 to move along all three axis). Shafts 100 support apparatus 10 and have linear bearings that move apparatus 10 therealong.

The pipette loading/dispensing cycle is repeated as many times as the user requires.

FIGS. 2 and 3 illustrate in more detail loading/stripping plate 16 modified in accordance with the teachings of the present invention. Stripper plate 16 includes a pair of pins 21 formed on the opposite, lower interior surfaces thereof and positioned to engage mating hooks, or slots, 23 formed on the standard carrier plate 18. A typical cylinder 26 is illustrated as being ready for positioning within one of the ninety-six apertures 25 formed in plate 16 as illustrated. A pair of elongated members, or box strippers 32 and 34 are fixedly secured to the opposite, lower interior surfaces of plate 16, and, as will be explained hereinafter, engage the upper surface of pipette tip box 19 to force, or strip, the pipette tips from pipette tip box 19 after the loading operation is completed. A single pipette tip 20 is shown in one of the apertures, or openings, 27 formed in the pipette tip box 19. The bottom surface of stripping plate 16 has a series of progressively thicker steps, or recesses, 31, 33, 35 . . . formed thereon as illustrated to form a plate of variable thickness.

The progressive steps reduce the amount of force required if all the pipette tips 20 are stripped from plate 16 at the same time. This configuration enables two rows of pipette tips 20 to be stripped at a time, the first two rows being stripped starting at the middle of box 19 (note that the steps are mirror images, or symmetrically sized, about the center-line of box 19). FIG. 3 illustrates in more detail two cylinders 26 engaging corresponding pipettes 20 through stripper plate 16 (two corresponding pistons 29 are also illustrated). After the dispensing operation is completed, the dispensing apparatus 10 is moved to the tray carrier location on deck A, the pipette tips 20 then being progressively stripped from the cylinders 26 by the progressively thicker recesses, 31, 33 . . . 35, the stripped pipette tips falling into pipette tip box 19 for disposal (note that for illustrative purposes, only recesses 31 are shown in the process of engaging the tops of pipette tips 20; in actuality, the other recesses will also engage the tops of adjacent pipette tips 20).

Apparatus 10 operates as follows:

The top mounted air cylinder 50 is similar in operation to the corresponding cylinder shown in the aforementioned patent except that the cylinder is modified to have three operating positions. Cylinder 50 provides the force required to load the pipette tips to the system cylinders. The added feature is the utilization of stroke limiter 51. This, in essence, causes air cylinder 50 to function as a three position device (up, mid, down). This is required as part of the pipette tip box 19 load cycle which is as follows:

The dispensing head assembly 10 moves in the X and Y axis so that it is in alignment with the tip box loading station as shown in FIG. 4 (the operator, or a robot, places tip box 19 in the carrier plate 18).

The head assembly 10 then moves down in the "Z" axis direction as shown in FIG. 5. The head assembly then moves back in the "Y" axis allowing pins 21 to be engaged with matching mating hooks, or slots, 23 on tray carrier 18 as shown in FIG. 6. Tray carrier 18 is now mechanically connected to the head dispensing assembly 10 by way of pins 21 and is free to move up/down from deck A with the head assembly 10 as shown in FIG. 7.

Air cylinder 50 is then activated, pulling stripper/loading plate 16 up (up position). Since the stripper plate 16 is mechanically connected to tray carrier 18, the tray carrier 18 also moves up. Since the cylinders are stationary with reference to stripper plate 16, the upward motion pulls the pipette tips 20 onto cylinders 26. In essence, actuator cylinder 50 extends and retracts and moves vertical shafts 12 and 14, the two sets of shafts moving in opposite directions to each other. Shafts 12 and 14 are connected to plates 24/30 and 16. As air cylinder 50 is activated and its piston moves in relationship to its cylinder, shafts 12 and 14 move in relationship to each other, causing the plates below actuator 50 to move. When air cylinder 50 is activated, shaft 12 moves upwardly. Cylinders 26 are mounted to plate 24 which in turn is attached to plate 30 which in turn is fixed to shaft 14. Shaft 14 is thus in essence attached to cylinders 26. When air cylinder 50 is activated, plate 16 and box carrier 18 move upwardly. Cylinders 26 are essentially fixed and the pipette tips 20 are forced onto cylinders 26.

At this point, the pipette tips 20 are sealed to the cylinders 26 and they are still in their box. Therefore, the pipette box 19 must be removed from the pipette tips 20. The pipette tips are available from a number of manufacturers. Some of these manufacturers mold their boxes with close or poor tolerances and when a load cycle is initiated, at least 500 lbs of force is applied to the pipettes 20 and the box 19. This tolerance problem may cause the pipettes to stick in the box 19. Therefore, the unloading mechanism must be able to strip both the pipettes from the cylinders and also be able to strip the pipette box 19 away from the pipettes 20.

The head assembly and the connected box 19 now move up (FIG. 8). This allows space between the bottom of the tray carrier 19 and deck A. This space is required for the box strip cycle. The large air cylinder 50 moves to its MID position (FIG. 9) which raises the pipettes 20 up and at the same time pushes the box 19 away with the aid of box strippers 32 and 34. The pipette tips 20 are firmly attached and sealed to cylinders 26 and free of the box 19. The head assembly can now move down ("Z" axis direction), placing tip box 19 and tray carrier 18 onto deck A.

The head assembly 10 can now move up in the "Y" axis (see FIG. 4) freeing its mechanical connection from the tray carrier 18, plate 16 and pins 21. Once free, head assembly 10 can now move about table, or deck, A in the X, Y and Z directions moving fluid into and out of microplates that are located on the deck A. FIG. 10, it should be noted, shows the pipette tips attached to the cylinders and the pipettes partially removed from the box. In essence, FIG. 10 shows the loading cycle. In the unload cycle described hereinafter, the motions are the same although reversed. For example, pipette tips 20 would be shown connected to their cylinders 26 in a corresponding version of FIGS. 4, 6 and 7. FIG. 10 would be modified to show the pipette tips 20 disconnected from their associated cylinders 26.

Since the head assembly is free to move in the X, Y and Z axis, expansion to larger deck surfaces with greater number of plates is possible. In addition, higher density plates can be accommodated. The standard microplate is made up of 96 apertures, or wells. However, the same size can be further divided to make 384 wells and further divided to 864. Since the head assembly moves in the X and Y axis like a gantry crane, it can move and fill all wells of the newer style plates. The 384 well variety will be filled with 4 dispenses (X, Y, Z, D dispense) and it will take 16 dispense cycles (X, Y, Z, D) to fill the 864 varity. The dispensing apparatus of the present invention is thus capable of being used with various type microplates.

After the completion of fluid movement from one microplate to others on the deck, pipette tips 20 will be removed from the cylinders. The pipette strip cycle works in the following sequence:

The head assembly 10 moves in the X and Y axis so that it is in alignment with the tip box loading station as shown in FIG. 4.

The head assembly, then moves down in the "Z" axis as shown in FIG. 5. The head moves back in the "Y" axis allowing the pins 21 to be engaged with the matching mating hooks 23 on tray carrier 18. (See FIG. 6).

The tray carrier 18 is now mechanically connected to the dispense head assembly 10 by way of the pins 21 and is free to move up/down with the dispense head assembly (See FIG. 7).

The head assembly and tray carrier 18 are now moved up in the "Z" axis allowing room between the tray carrier bottom and the deck A.

The large air cylinder 50 is then activated to the "low" position, the cylinders 26 being stationary with reference to the stripper plate 16. The stripper plate 16 moves down, the pipettes 20 being stripped away from the cylinders 26 progressively through the use of progressively thicker recesses 31, 33 . . . 35 and falling into the pipette tip box 19.

The head assembly 10 is now moved away from the tray carrier 18 using the X, Y and Z axis. Once the head assembly is away from the tray carrier 18, the used pipette tip box 19 can be removed and replaced with another one, the entire system thus lending itself to automation. A robot can be integrated into the system by providing microplates as well as adding new pipette tip boxes. An automated system has the capability of maintaining these cycles operating for relatively long time periods.

It should be noted that tip box 19 is free to move (slide) in the horizontal direction, forwards and backwards, within tray carrier 18 (indicated by reference arrows 40). This motion is necessary for the load and unload cycles when the pipettes are attached to the cylinders. Specifically, when head assembly 10 moves, the pipettes drag the box 19 back and forth as necessary so that pins 21 clear tray carrier 18.

Apparatus 10 can be moved along deck A in an X, Y and Z direction allowing fluid to move from tray to tray as well as loading/unloading pipette tips from various stations located on deck A.

It should be noted that a plurality of tip load/unload stations could be provided to allow pipette tips to be reused that were used for specific applications thus saving the cost involved in pipette tip disposal.

The present invention thus combines the use of a unique liquid dispensing apparatus with a conventional pipette tip box carrier plate to provide an apparatus which enables the apparatus to be adaptable for robotics and automation.

While the invention has been described with a reference to its preferred embodiment, it will be understood by those skilled in the art that various changes may be made and equivalents may be substituted for elements thereof without departing from the true spirit and scope of the invention. In addition, modifications may be made to adapt a particular situation or material to the teachings of the invention without departing from its essential teachings.

What is claimed is:

1. Apparatus for dispensing predetermined amounts of liquid into receptacles comprising:

first and second sets of vertically extending shafts;

a first plate member coupled to said first and second set of shafts;

actuator means positioned on said first plate member;

a pipette tip box for supporting a plurality of pipette tips;

a carrier tray for supporting said tip box and having means for receiving engagement members;

a loading/stripping plate member having a bottom surface movable along said second set of shafts, said loading/stripping plate member having said engagement members formed thereon for engaging said means for receiving engagement members;

a second plate member supporting a plurality of dispensing cylinders, said second plate member being fixedly connected to said first set of shafts; and means to energize said actuator means whereby said loading/stripping plate member is moved upwardly by said second set of vertically extending shafts in a manner such that each pipette tip is positioned into sealing engagement with an adjacent vertically aligned dispensing cylinder.

2. The apparatus of claim 1 wherein said actuator means is energized in a manner whereby said loading/stripping plate member is moved in the downward direction by said second set of vertically extending shafts causing each pipette tip to be pushed off the corresponding cylinder to which it is sealed.

3. The apparatus of claim 1 further including a third plate member movable by said second set of vertically extending shafts having a plurality of piston members supported therein, each of said piston members being positioned for upward or downward movement within one of said adjacent and vertically aligned dispensing cylinders.

4. The apparatus of claim 3 further including actuator means for moving said third plate member in an upwards direction whereby said liquid is drawn into said pipette tips.

5. The apparatus of claim 4 wherein said actuator means moves said third plate member in a downwards direction whereby said liquid is dispensed into said receptacles.

6. The apparatus of claim 1 wherein said actuator means is energized in a manner whereby said loading/stripping plate member is moved downwardly by said second set of vertically extending shafts such that said pipette tip box is forced away from the pipette tips sealed to said cylinders.

7. The apparatus of claim 6 wherein said loading/stripping plate member comprises means on said bottom surface for contacting the top surface of the pipette tip box as said loading/stripping plate member moves downwardly, said contacting means forcing said pipette tip box away from said pipette tips sealed to said cylinders.

8. The apparatus of claim 6 wherein said loading/stripping plate member comprises a substantially planar shape having a predetermined length and width, edge portions and a center portion, said loading/stripping plate member having a plurality of apertures formed therein for receiving said dispensing cylinders, the thickness of said loading/stripping member varying along a portion of said predetermined length.

9. The apparatus of claim 8 wherein the thickness of said loading/stripping member decreases stepwise from the edge portions to the center portion of said loading/stripping plate member.

10. The apparatus of claim 1 further including means for enabling said loading/stripping plate member to initially engage said means for receiving engagement members.

* * * * *